United States Patent
Scheer

(10) Patent No.: US 7,735,748 B1
(45) Date of Patent: Jun. 15, 2010

(54) SPRAY NOZZLE WITH IMPROVED TIP AND METHOD OF MANUFACTURE

(76) Inventor: Ingo Werner Scheer, 6455 La Jolla Blvd., La Jolla, CA (US) 92037

( * ) Notice: Subject to any disclaimer, the term of this patent is extended or adjusted under 35 U.S.C. 154(b) by 185 days.

(21) Appl. No.: 11/545,282

(22) Filed: Oct. 10, 2006

(51) Int. Cl.
*A62C 5/02* (2006.01)
*A62C 5/00* (2006.01)
*B05B 1/28* (2006.01)
*A61M 11/02* (2006.01)
*B23K 9/00* (2006.01)
*H02G 3/18* (2006.01)
*B21K 21/08* (2006.01)

(52) U.S. Cl. .................. 239/8; 239/398; 239/290; 239/371; 219/121.47; 219/121.51; 174/59; 29/890.142; 29/890.143

(58) Field of Classification Search .......... 239/690, 239/696, 398, 434.5, 399–434, 8, 290, 371, 239/690.1, 704, 706; 219/121.47, 121.51; 174/59; 29/890.142, 890.143
See application file for complete search history.

(56) References Cited

U.S. PATENT DOCUMENTS

| | | | | |
|---|---|---|---|---|
| 1,736,356 A * | 11/1929 | Mueller | .................. | 239/300 |
| 3,401,883 A * | 9/1968 | Gebhardt et al. | ............. | 239/690 |
| 4,031,854 A * | 6/1977 | Sprague, Jr. | ................. | 118/641 |
| 4,098,632 A * | 7/1978 | Sprague, Jr. | ................. | 156/295 |
| 4,225,086 A * | 9/1980 | Sandell | ...................... | 239/428 |
| 4,478,370 A * | 10/1984 | Hastings | ...................... | 239/707 |
| 4,765,271 A * | 8/1988 | Jochem et al. | ............... | 118/405 |
| 5,188,290 A * | 2/1993 | Gebauer et al. | ................. | 239/3 |
| 5,685,482 A * | 11/1997 | Sickles | ........................... | 239/3 |
| 5,692,886 A * | 12/1997 | Kobayashi et al. | ..... | 417/423.12 |
| 5,697,559 A * | 12/1997 | Davis et al. | .................. | 239/703 |
| 5,704,554 A * | 1/1998 | Cooper et al. | ............ | 239/690.1 |
| 5,765,761 A * | 6/1998 | Law et al. | ................ | 239/690.1 |
| 5,845,846 A | 12/1998 | Watanabe | | |
| 5,868,322 A * | 2/1999 | Loucks et al. | ................ | 239/418 |
| 6,012,647 A * | 1/2000 | Ruta et al. | .................... | 239/132.1 |
| 6,032,876 A * | 3/2000 | Bertsch et al. | .............. | 239/418 |
| 6,056,213 A * | 5/2000 | Ruta et al. | .................... | 239/337 |
| 6,147,347 A * | 11/2000 | Hirabayashi et al. | ........ | 250/288 |
| 6,322,011 B1 * | 11/2001 | Allen | .......................... | 239/703 |
| 6,461,361 B1 | 10/2002 | Epstein | | |
| 6,729,334 B1 * | 5/2004 | Baran | ..................... | 128/207.14 |
| 6,817,555 B2 * | 11/2004 | Reichler et al. | ............. | 239/700 |
| 6,899,289 B2 | 5/2005 | McCracken | | |
| 7,141,788 B2 * | 11/2006 | Hirabayashi et al. | ........ | 250/288 |
| 7,296,760 B2 * | 11/2007 | Alexander et al. | .......... | 239/301 |
| 2006/0124780 A1 * | 6/2006 | Cooper | ....................... | 239/690 |
| 2008/0237372 A1 * | 10/2008 | Scheer | ....................... | 239/418 |

* cited by examiner

*Primary Examiner*—Len Tran
*Assistant Examiner*—Steven M Cernoch

(57) ABSTRACT

The invention provides a compact spray nozzle having an improved tip for reproducibly forming droplets from small amounts of liquid with improved operational stability and spray pattern quality compared to prior art atomizing devices. The invention further provides a method for manufacturing the nozzle tip by machining comprising the step of machining the orifice and the inner section and/or the centering section in one setup.

14 Claims, 6 Drawing Sheets

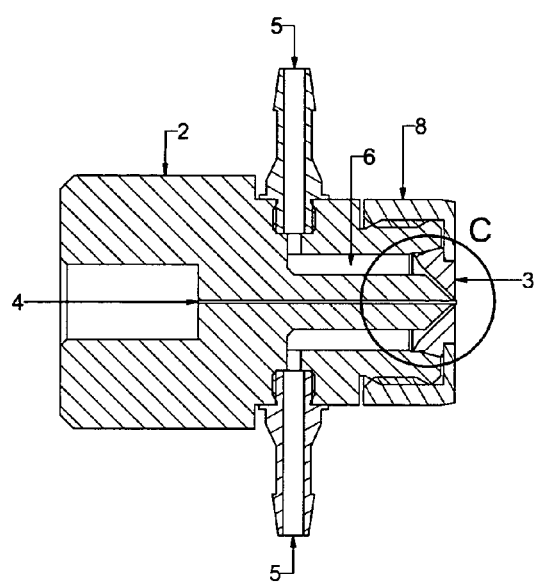
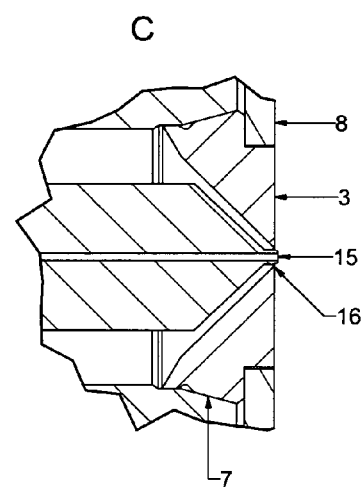
FIG. 3A
FIG. 3B

SPRAY NOZZLE WITH IMPROVED TIP AND METHOD OF MANUFACTURE

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

1. Field of Invention

The present invention relates to a spray nozzle having an improved tip and its method of manufacture for providing a repeatable performance in terms of droplet size and spatial droplet distribution. The invention is particularly suitable for the fine atomization of small amounts of liquids.

2. Background of the Invention

Spray nozzles are used to spray small amounts of liquids in various applications, such as medical nebulizers, chemical analysis of liquid samples, spray drying and coating medical devices.

Such spray nozzles generally comprise a body with a liquid line and a removable tip having a central orifice provided at the atomizing end, which extends to an inner section. The spray nozzle may also include one or more passages for an atomizing fluid, which may be expelled through an annular gap or gas annulus provided between the body orifice and the tip orifice to disintegrate the liquid. Spray nozzles using compressed gas to disintegrate a liquid are also referred to as twin-fluid nozzles.

Optimum atomization and particle transport efficiencies generally depends on the spatial characteristics of the spray plume and on the droplet size which, in turn, depends on the roundness of tip orifice and concentricity between the tip orifice and inner section. This is particularly true, when an atomizing gas is provided through a comparatively small annular gap, which often has a width on the order of only 20 to 250 micrometers.

However, the lack of concentricity between the inner section and orifice of the tip is a common problem of prior art spray nozzles having comparatively small orifices. FIG. 1 depicts an enlarged view of a tip of an exemplary spray nozzle having a conical inner section extending to an orifice. It can be seen that the orifice 16 of the tip 3 is not concentric with respect to the inner surface 72 of the tip. In this example there is an eccentricity of 0.04 mm between axis of inner section 71 and axis of tip orifice 70.

Inner section-orifice eccentricity may result from machining the orifice and inner section of the tip in different setups. A further problem associated with conventional atomizing devices are imperfections of the orifices in terms of roundness and surface quality. The orifices are generally manufactured using conventional manufacturing procedures such as drilling. For instance, drilling of small holes can lead to spiral marks and burrs and may require secondary procedures such as electropolishing which, in turn, may result in manufacturing tolerance variations and/or out-of-roundness of the orifice. When manufacturing a series of spray nozzles comprising comparatively small orifices using current machining procedures the reproducibility within a badge may therefore not be assured. In addition, with current spray nozzles there is a risk of misalignment during disassembling and reassembling of the nozzle resulting in poor concentricity of the body in relation to the tip orifice. Thus, devices, even of the same type, often will have different spray characteristics resulting from very minor variations in terms of concentricity of tip orifice and inner section, orifice roundness and surface quality. To visualize the effect of an eccentricity between inner section of tip and tip orifice on the spray characteristics of a twin-fluid nozzle, the velocity distribution of the fluid exiting the tip orifice has been simulated using Computational Fluid Dynamics (CFD) software. FIG. 2A is a scalar representation and FIG. 2B is a vector representation of the fluid exiting the annular gap. Despite the optimum roundness and equal width of the tip orifice, there is an inhomogeneous velocity distribution at the annular gap, which is caused by a small eccentricity between the inner section of the tip and the tip orifice.

The spray performance in terms of symmetric spatial droplet distribution and tight droplet size distribution of spray nozzles is closely related to the roundness and concentricity of tip orifice and inner section of tip. In case of twin-fluid atomizers, any imperfection and eccentricity between the axes of the liquid orifice and the tip can cause the flow of the atomizing gas to be cylindrically asymmetric with respect to the axis of the liquid exiting from the liquid orifice. Hence, inhomogeneous gas velocities within the annular gap, as illustrated in FIGS. 2A and 2B, will lead to nebulization by the atomizing gas that is different on different sides of the spray plume. Consequently, poor spray stability and droplets that are too large and polydisperse in size may result in poor reproducibility and often poor stability during operation which, in turn, may lead to coating defects or reduced sample analysis efficiency.

OBJECT OF THE INVENTION

Accordingly, there is a need for a spray nozzle comprising an improved tip to atomize small liquid amounts that overcomes the aforementioned problems with the prior art and provides a homogeneous spatial droplet distribution, a tight droplet size distribution and an improved stability and reproducibility of precision spraying processes.

One object is to provide a spray nozzle to atomize small liquid amounts having a compact and robust design that can be manufactured reproducibly, resulting in a repeatable performance from one spray nozzle to the next.

Another object is to provide a spray nozzle, which ensures the concentric alignment of the body in relation to the tip to reproducibly generate a uniform spray pattern.

Yet another object is to provide a cost-effective manufacturing method for machining the tip orifice, the inner surface of the tip and the centering section between nozzle body and tip.

Still another object is to allow repeatable assembling and disassembling of the tip and thereby ensuring proper alignment of the tip orifice relative to the body.

These and additional features and advantages of the invention will be more readily apparent upon reading the following description of exemplary embodiment of the invention and upon reference to the accompanying drawings herein.

SUMMARY

In one embodiment, a device to disintegrate a liquid into fine droplets is provided comprising a body having an entrance end and an exit end for a first fluid and a tip having an inner section extending to an orifice through which a second fluid is expelled. The tip is provided at the atomizing end and essentially coaxial with the body such that an intermediate space is formed between the body and tip. At least a portion of the inner section of the tip is machined in the same setup as the orifice so that the axis of the orifice is concentric with the axis of the machined inner section. In certain embodiments, the tip may be machined by internal turning and the orifice diameter of the tip may be smaller than 2 mm. Also, the machined portion of the inner section may be used to align the tip in relation to the body. The tip may further comprise a centering section to align the tip in relation to the body being machined in the same setup as inner section and orifice of tip. The inner section of the tip may have a conical shape. The first fluid may be a liquid and the second fluid a gas. Alternatively, the first fluid may be a gas and the second fluid a liquid.

In a further embodiment, a device to disintegrate a liquid into fine droplets is provided comprising a nozzle tip having an inner section extending to an orifice that is smaller than 2 mm through which the fluid is expelled, wherein at least a portion of the inner section is machined in the same setup as the orifice so that the axis of the orifice is concentric with the axis of the inner section. In certain embodiments, at least a portion of the inner section is machined by internal turning.

In another embodiment, a method is provided for manufacturing a nozzle tip having an inner section extending to an orifice with an diameter of up to 2 mm, comprising the step of machining the orifice and at least a portion of the inner section of the nozzle tip in the same setup by internal turning so that the axis of the orifice is concentric with the axis of the inner section.

In still another embodiment, a method for manufacturing a device to disintegrate a liquid into fine droplets having a body with a centering section and a tip with an orifice diameter up to 2 mm, comprising the steps of machining the tip orifice and at least a portion of the centering section of the tip in the same setup by turning so that the axis of the orifice is concentric with the axis of the centering section of the tip and assembling the body and the tip such that the centering section of the tip mates with the centering section of the body.

DRAWINGS

The accompanying drawings, which are incorporated in and constitute a part of this specification, serve to explain the principles of the invention. The drawings are in simplified form and not to precise scale.

FIG. 3A is a longitudinal cross-sectional view of an twin-fluid atomizer;

FIG. 3B is a longitudinal cross-sectional expanded view of the atomizer tip of FIG. 3A;

BRIEF DESCRIPTION OF THE DRAWINGS/PREFERRED EMBODIMENTS

Figure 1:
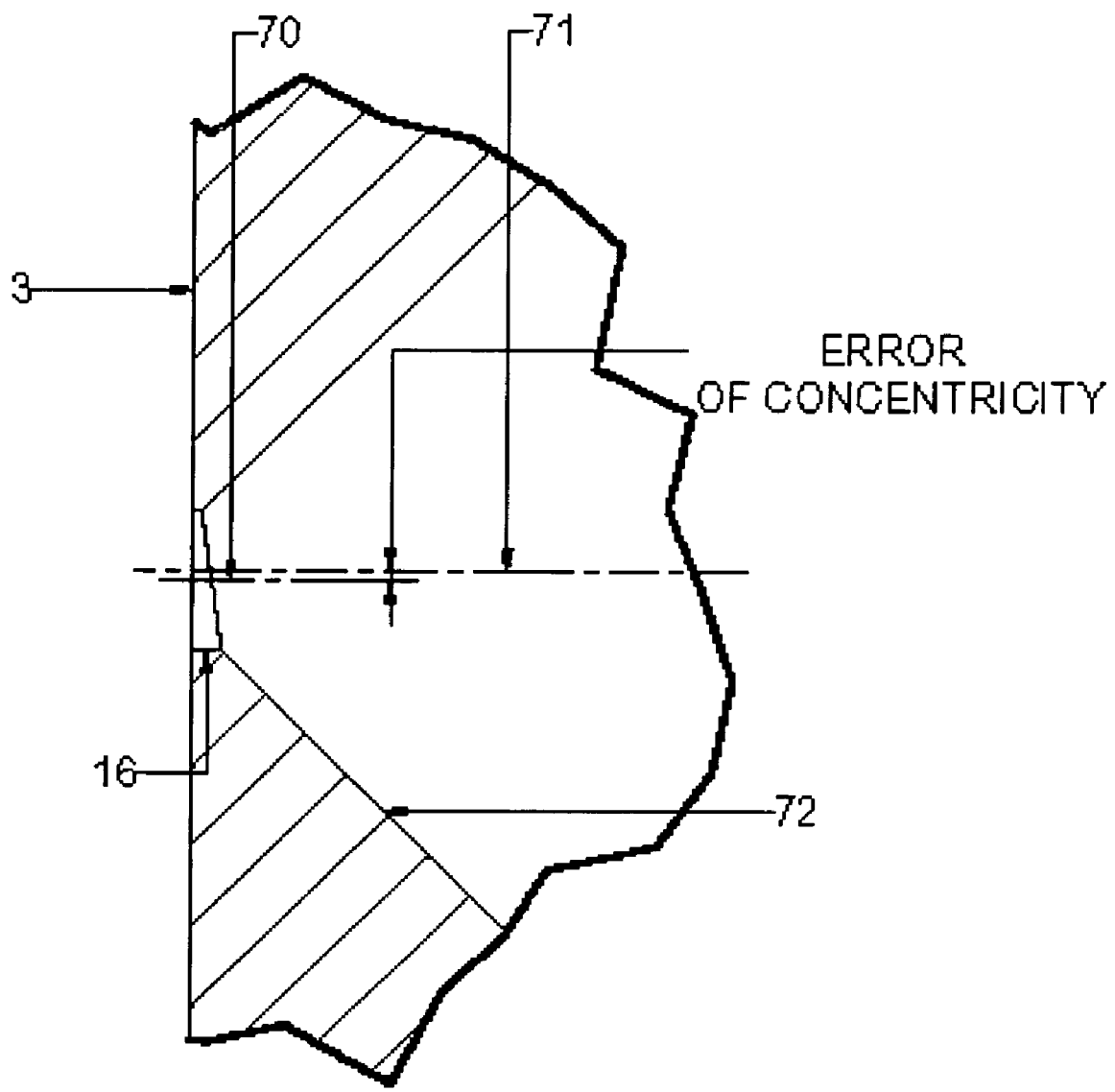
FIG. 1 (Prior Art) is a longitudinal cross-sectional detail view of a nozzle tip comprising an orifice and an inner section.
Figure 2A:
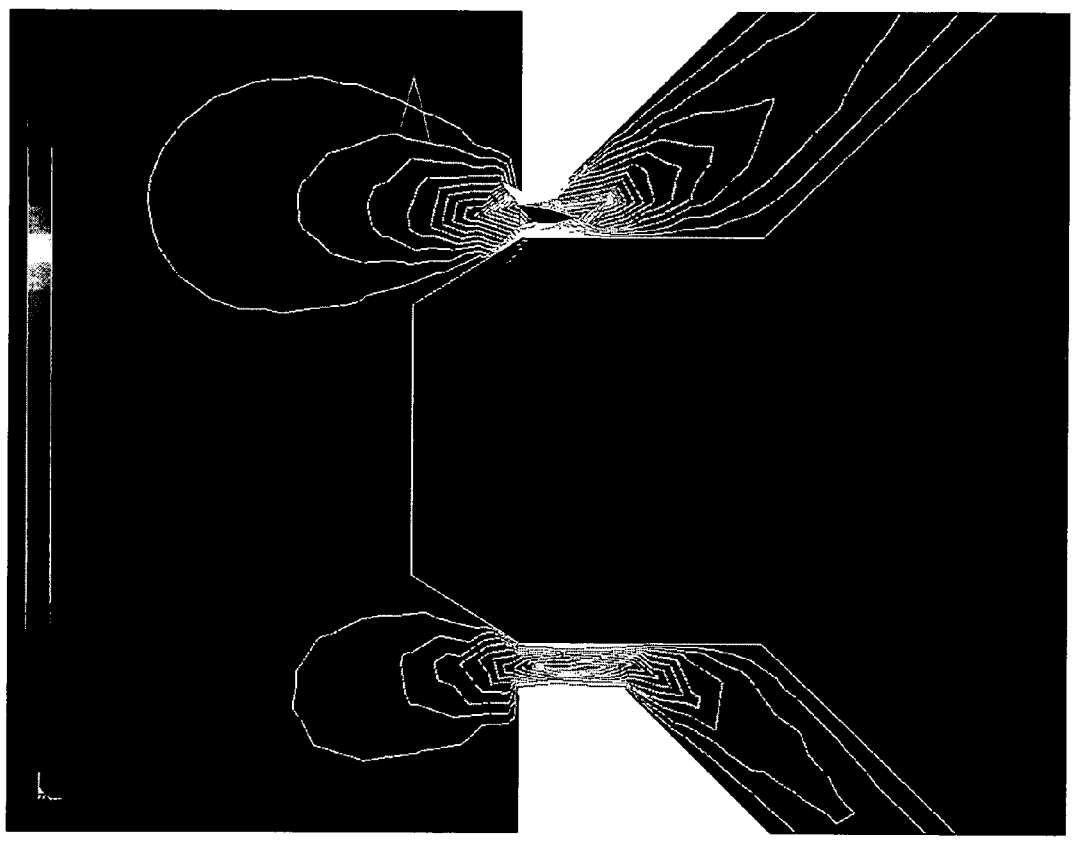
FIG. 2A (Prior Art) is a Computational Fluid Dynamics simulation (scalar representation) of the velocity distribution at an nozzle orifice.
Figure 2B:
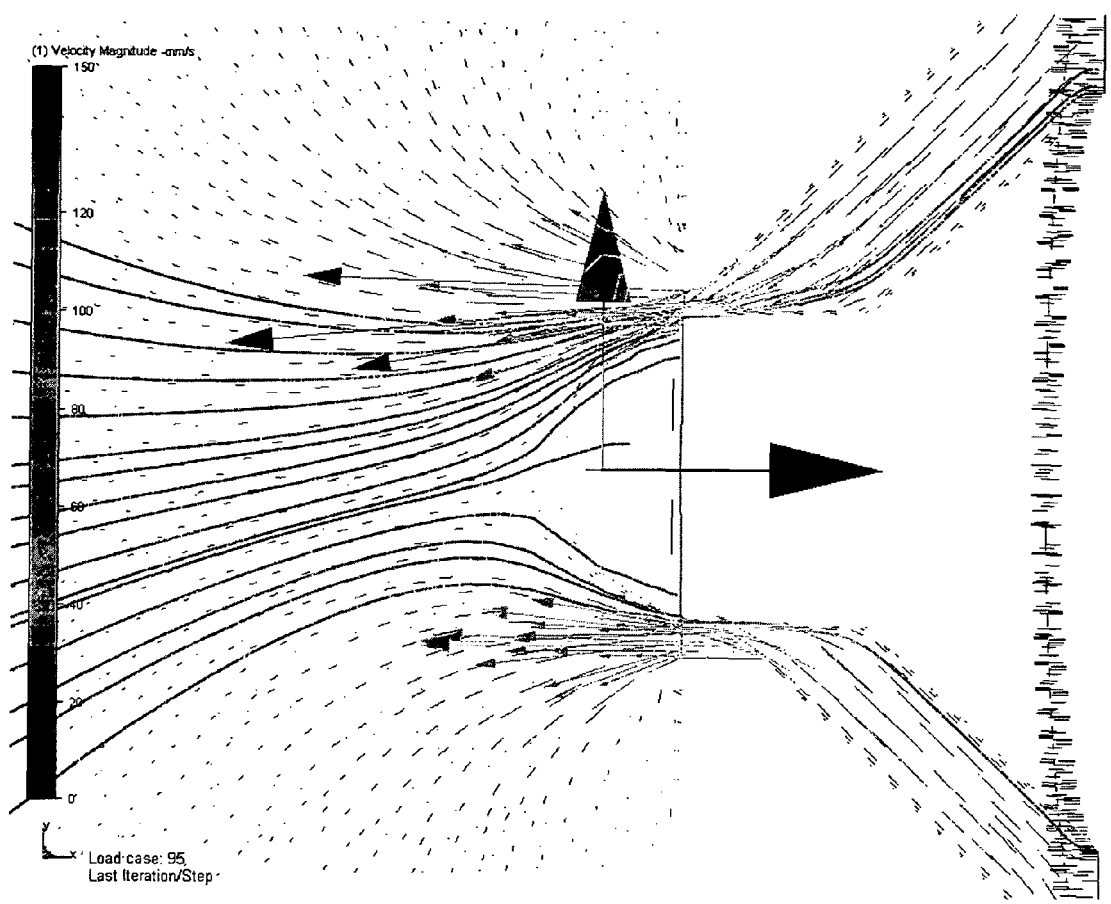
FIG. 2B (Prior Art) is a Computer Fluid Dynamics simulation (vector representation) velocity distribution at an nozzle orifice.

The invention provides a compact spray nozzle for reproducibly forming droplets from small liquid amounts comprising a tip with improved accuracy providing improved operational stability and reliability compared to prior art atomizing devices. The spray nozzle has a body comprising a central fluid line for the fluid to be disintegrated and a tip having a central orifice provided at the atomizing end. The tip is removably secured and aligned through a centering section, so that a concentric alignment between the body and the tip orifice and a repeatable assembly and disassembly can be provided.

The spray nozzle may also include one or more passages for an atomizing fluid, which is expelled through an annular gap or gas annulus provided between the body orifice and the tip orifice to disintegrate the liquid. The spray nozzle is designed to allow precise and repeatable machining of the inner surface of the tip, the centering section between tip and body and the tip orifice to ensure optimized concentricity and surface quality of the atomizing end.

The invention further provides a method for manufacturing the nozzle tip by machining the orifice and the inner section and/or the centering section in one setup.

DETAILED DESCRIPTION

While the invention will be described in connection with certain embodiments, it will be understood that the invention is not limited to these embodiments. On the contrary, the invention includes all alternatives, modifications and equivalents as may be included within the spirit and scope of the present invention. Details in the Specification and Drawings are provided to understand the inventive principles and embodiments described herein, to the extent that would be needed by one skilled in the art to implement those principles and embodiments in particular applications that are covered by the scope of the claims. All dimensions used herein are suggestive and not intended to be restrictive.

FIG. 3A is a longitudinal cross-sectional view of an exemplary spray nozzle or atomizer of the present invention. An expanded view of the tip region of the nozzle is provided in FIG. 3B.

The atomizer comprises body 2 and tip 3 being secured to the atomizing end to permit passage of gas. The body includes a central fluid line, which extends from the fluid inlet 4 to the fluid orifice 15. The diameter of orifice 15 may range between approximately 0.05 and 0.5 mm depending on the particular application. The tip 3 is secured by securing ring 8 such that a small annular gap 16 to permit passage of gas therethrough from the fluid passages 6 is provided between the tip orifice and body. It has preferably a tapered inner section extending to a central orifice 16. Alternatively, the inner section of the tip may have a hemispherical or cylindrical shape. The diameter of the tip of the body and the orifice diameter of the tip defines the width of the annulus. The nozzle body is preferably made from a metallic material such as stainless steel. Alternatively, a polymeric material such as PEEK can be used. The tip is preferably made from a metallic material such as stainless steel, titan and the like. Other tips with various geometries may be provided to adapt the atomizer for specific applications. The tip may further comprise additional bores to provide various spray patterns such as a flat spray. The atomizer is connected via fluid inlet 4 to means to supply the liquid to be atomized such as a pump coupled to a supply container and via fluid inlets 5 to means to supply the atomizing gas.

In operation, the liquid to be atomized is supplied through the inlet 4. The atomizing fluid (compressed gas) is fed in the inlets 5, travels through the passages 6 extending from fluid inlets 5 via a portion substantially coaxial to the liquid line and a conical portion and exits the atomizer trough the annular gap 16. The liquid flows from fluid inlet port 4 through the fluid line to the atomizing end and exits orifice 15. The liquid is disintegrated into fine droplets by the atomizing gas when it exits orifice 15. Liquid and carrier gas is mixed outside the atomizer to obtain an aerosol.

In an further embodiment, the liquid to be atomized may be supplied through the fluid inlet, travel through the fluid passages extending from fluid inlet via a portion substantially coaxial to the fluid line and a conical portion and exit the atomizer trough the annular gap formed between the body orifice and tip orifice. The atomizing fluid (compressed air) may flow from one or more fluid inlet ports through an inner fluid line to the atomizing end of the nozzle body where it exits the orifice.

In still another embodiment, electrostatic means may be furthermore provided to assist the liquid disintegration process. A high voltage source may be electrically connected to the liquid conduit of the nozzle, while portions of the nozzle are electrically isolated from the liquid conduit.

To ensure that the center of the fluid orifice 15 runs coaxial to the center of the annular gap 16 there is provided a centering section to align the tip in relation to the body, as depicted in FIG. 3B by arrow 7. Thus, tip 3 can be easily removed for maintenance and cleaning of the atomizer without the risk of misalignment between the tip and body.

To maximize surface finish and concentricity, the following manufacturing procedure is adopted. In a first step, a central bore is drilled having a smaller diameter than the finished orifice. Next, as illustrated in FIG. 4 tip orifice 16, inner surface 72 and centering section 35 are machined in one setting. Tip orifice 16 and inner surface of the tip may be machined by internal turning and centering section 35 by external turning. Alternatively, the inner surface of the tip and the orifice may be machined by grinding or by boring out.

Figure 4A:
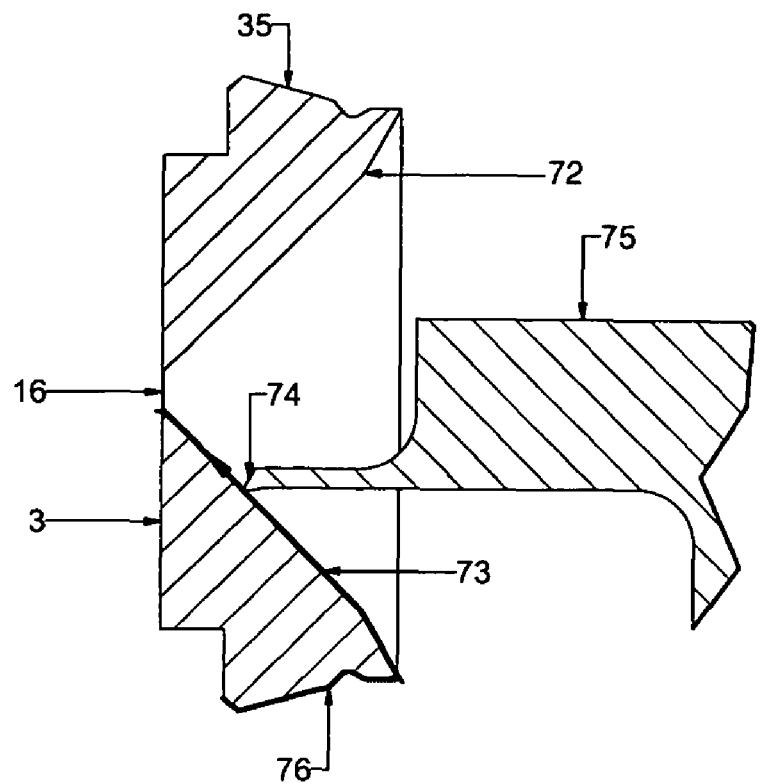
FIG. 4A is a longitudinal cross-sectional view of the atomizer tip of FIG. 3 showing the machining path during a turning operation.
Figure 4B:
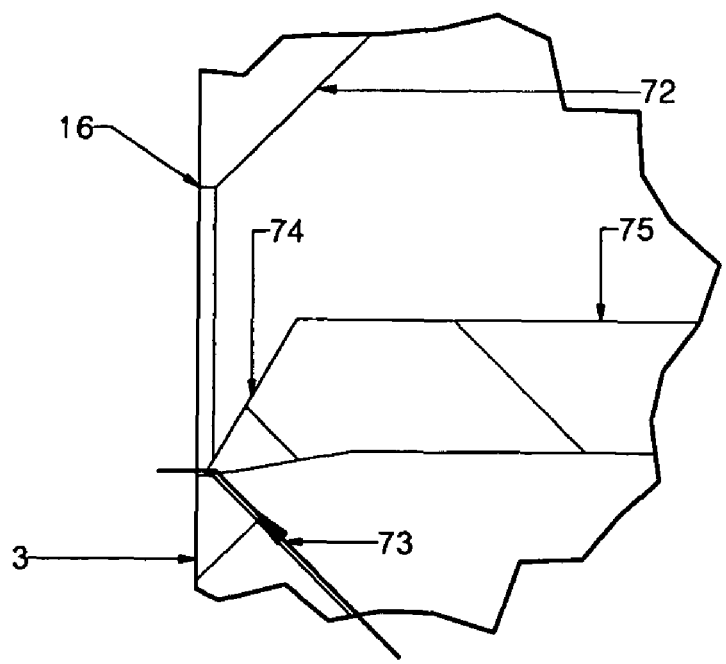
FIG. 4B is a expanded view of the atomizer tip of FIG. 3.

FIG. 4A is an enlarged view of an exemplary atomizer tip 3 during the final machining operation shown in more detail in FIG. 4B. The final machining path or machined section of the inner surface of the atomizer tip is illustrated by line 73. A small bore tool 75 having cutting edge 74 may be used to perform the machining operation. Machined section 73 extends from the inner tapered section to the orifice. Thus, a smooth transition between the tapered section of tip and tip orifice 16 is provided. By machining the inner surface of the tip 72 including the tip orifice in one setup a superior quality is obtained in terms of concentricity, roundness and smooth finish of inner section and orifice of tip as well as annular gap. In addition, a secure connection and optimized alignment between body orifice 15 and tip 3 is provided. The concentricity between the axis of body orifice 15 and the axis of orifice 16 of tip 3 is substantially optimized compared to prior art atomizers.

A repeatable and cost-effective manufacturing method of the nozzle tip is provided by machining the sections that are critical for the spray performance in the same setup. Thus, timesavings and an improved accuracy of the atomizer can be achieved compared to machining operations comprising several setups.

In order to demonstrate the performance of the spray nozzle of the present invention various spray tests have been conducted. The spatial droplet distribution of the twin-fluid nozzle, depicted in the embodiment of FIG. 3, has been measured and compared to an exemplary twin-fluid nozzle known by the prior art. The prior art nozzle has an annular hap with a homogeneous width and a small eccentricity between axis of inner section and axis of tip orifice as shown in FIG. 1. The spray pattern was measured 20 mm downstream from the nozzle orifice using an Optical Patternator. The liquid to be atomized (DI Water) was supplied by a syringe pump (manufactured by Hamilton Company, Reno, Nev.) at a flow rate of 15 ml/h. The gas was fed into the atomizing device at a pressure of 0.7 bar.

Figure 5:
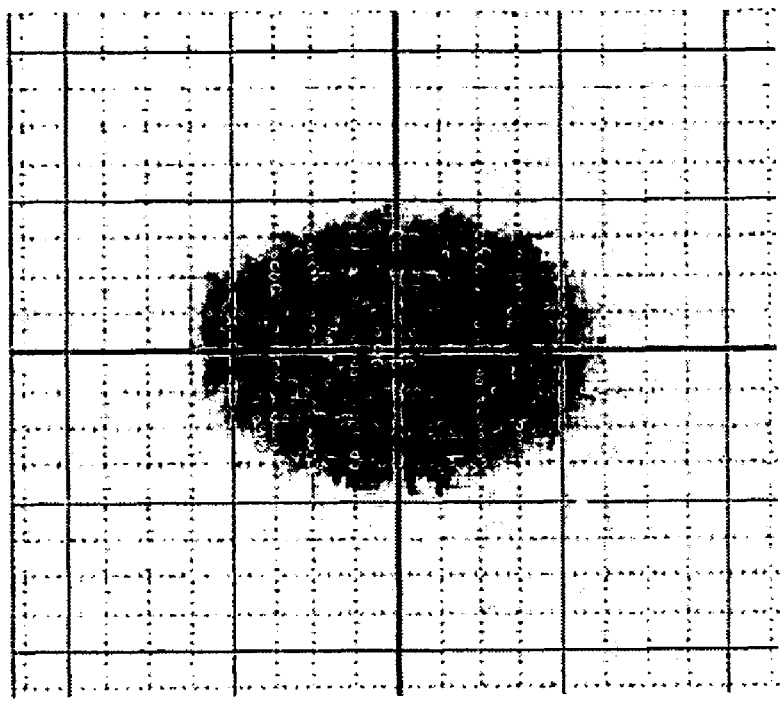
FIG. 5 (Prior Art) is a spatial droplet distribution generated by a conventional spray nozzle.

FIG. 5 depicts the spray pattern of the prior art spray nozzle. The spray pattern has an asymmetric spray distribution comprising coarse particles in the right portion. The asymmetric spray distribution results from inhomogeneous gas velocities within the annular gap caused by the error in concentricity between the tip orifice and inner section as discussed before.

Figure 6:
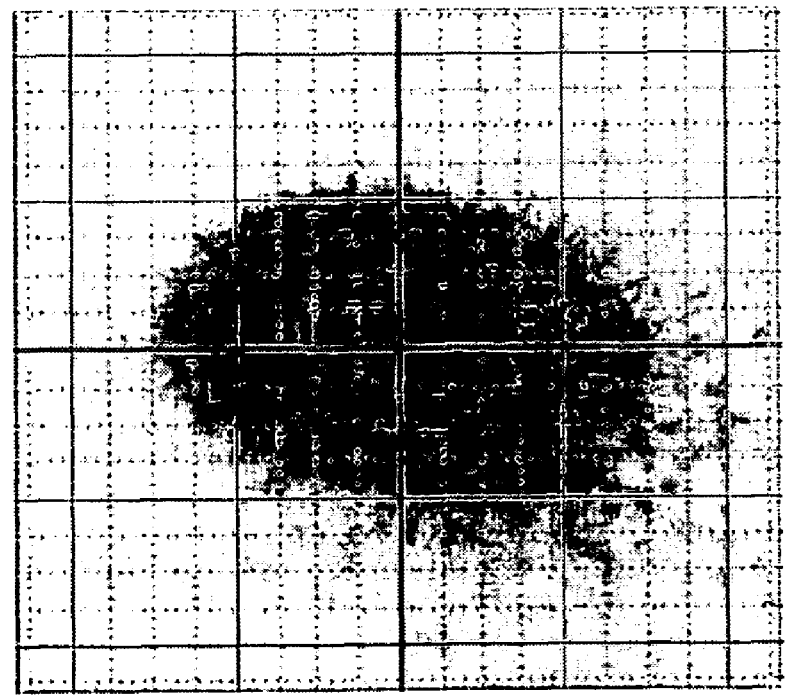
FIG. 6 is a spatial droplet distribution generated by the spray nozzle of the present invention.

In contrast, the spray pattern of the atomizer of the present invention has a homogeneous spatial droplet distribution as depicted in FIG. 6.

The results outline the advantages of the design and manufacturing methodology of the atomizer of the present invention in terms of spray pattern quality. The liquid atomization process has been improved by optimizing the atomization region in terms of concentricity between tip orifice and inner section of tip and concentricity between the axis of body and the axis of tip. In addition, there is provided an improved surface quality and a securing mechanism that prevents misalignment. Thus, a homogeneous spray pattern having a homogeneous droplet distribution can be obtained.

The invention claimed is:

1. A method for manufacturing a tip of a micro nozzle for producing a spray with a homogenous spatial droplet distribution having an orifice with a diameter of up to 2 mm and an inner section extending to the orifice comprising the steps of:
    forming a central cavity within the tip having a smaller size in the orifice section than the finished orifice; and
    performing a shaping operation of the orifice and of at least a portion of the inner section extending to the orifice in the same setup,
    whereby
    a smooth transition between the orifice and the inner section extending to the orifice is obtained and the longitudinal axis of the orifice is substantially concentric with the longitudinal axis of said portion of the inner section extending to the orifice so that the error of concentricity is less than 0.02 mm.

2. The method according to claim 1, wherein the inner section is used to align the tip in relation to a micro nozzle body.

3. The method according to claim 1, wherein the tip further comprising a step of shaping a centering section to align the tip in relation to a micro nozzle body.

4. The method according to claim 1, wherein the inner section of the tip extending to the orifice is conically shaped.

5. The method according to claim 1, wherein the shaping operation of the orifice is performed by internal turning.

6. The method according to claim 1, wherein the shaped portion of the nozzle tip is used as centering section to align a micro nozzle body and the tip.

7. The method according to claim 1, wherein the orifice is shaped so that an annular gap between 20 and 250 micrometers is formed between a micro nozzle body and the tip.

8. The method according to claim 1, wherein the portion of the inner section of the tip leading to the orifice and the orifice are shaped by turning.

9. The method according to claim 1, further comprising the step of using the micro nozzle for reproducibly forming droplets from small liquid amounts by feeding a first fluid into an entrance end of a body and a second fluid into an intermediate space extending to an annular gap formed between body and tip and disintegrating the liquid.

10. The method according to claim 9, wherein the first fluid is a liquid and the second fluid is a gas.

11. The method according to claim 9, wherein the first fluid is a gas and the second fluid is a liquid.

12. The method according to claim 9, further comprising the step of using electrostatic means to disintegrate the liquid.

13. The method according to claim 9, wherein the spray is applied to a medical device to form a coating.

14. The method according to claim 9, wherein the spray is dried to form particles.

* * * * *